(12) United States Patent
Carron et al.

(10) Patent No.: US 8,360,774 B2
(45) Date of Patent: Jan. 29, 2013

(54) PROPHY ANGLE

(75) Inventors: Chris J. Carron, Bloomsdale, MO (US); David G. Grither, Ste. Genevieve, MO (US)

(73) Assignee: Angstrom Manufacturing, Inc., Bloomsdale, MO (US)

( * ) Notice: Subject to any disclaimer, the term of this patent is extended or adjusted under 35 U.S.C. 154(b) by 672 days.

(21) Appl. No.: 12/196,891

(22) Filed: Aug. 22, 2008

(65) Prior Publication Data

US 2008/0311541 A1    Dec. 18, 2008

Related U.S. Application Data

(63) Continuation of application No. 11/189,193, filed on Jul. 26, 2005, now Pat. No. 7,422,433.

(51) Int. Cl.
*A61C 3/06* (2006.01)
*A61C 1/12* (2006.01)
*A61C 17/16* (2006.01)
*A61C 17/22* (2006.01)
*A61C 17/24* (2006.01)

(52) U.S. Cl. .................................. 433/125; 433/133

(58) Field of Classification Search ............... 433/112, 433/125, 126, 103, 114, 115, 116, 118, 124, 433/130, 131, 133, 165, 166; 606/78–83, 606/167, 780; 173/216, 217; 81/57.13, 57.29; 74/425, 423, 409, 417; 384/244, 245
See application file for complete search history.

(56) References Cited

U.S. PATENT DOCUMENTS

| | | | |
|---|---|---|---|
| 623,469 A | 4/1899 | Hailer | |
| 1,170,524 A | 2/1916 | Fernald | |
| 1,199,823 A * | 10/1916 | Sadtler | 81/57.29 |
| 1,301,472 A * | 4/1919 | Macecevic | 81/57 |
| 1,333,809 A | 3/1920 | Laurer | |
| 1,379,880 A | 5/1921 | Seaborn | |
| 1,688,136 A | 10/1928 | Chayes et al. | |
| 1,999,488 A | 4/1935 | Swisher et al. | |
| 2,025,779 A | 12/1935 | Roelke | |
| 2,147,832 A * | 2/1939 | Drexler | 74/423 |
| 2,229,509 A * | 1/1941 | Koza | 74/423 |
| 2,284,871 A * | 6/1942 | Huss | 81/57.29 |
| 2,319,465 A * | 5/1943 | McCombs | 74/423 |
| 2,400,912 A | 5/1946 | Britt et al. | |
| 2,438,291 A * | 3/1948 | Koza | 74/423 |
| 2,462,647 A * | 2/1949 | Koza | 74/417 |
| 2,582,336 A * | 1/1952 | Koza | 74/416 |
| 2,589,822 A * | 3/1952 | Kostka | 74/417 |

(Continued)

OTHER PUBLICATIONS

US 5,883,201, 03/1999, Salem (withdrawn)

*Primary Examiner* — Todd Manahan
*Assistant Examiner* — Michael R Ballinger
(74) *Attorney, Agent, or Firm* — Steven M. Greenberg, Esq.; Carey, Rodriguez, Greenberg & O'Keefe

(57) ABSTRACT

The present invention provides a dental prophylaxis angle that includes a housing, a drive shaft, and a rotor. The housing may define a first bore and a second bore in communication with the first bore. The drive shaft is positionable in the first bore and may include a distal bearing surface. The rotor is positionable in the second bore and can be driven by the drive shaft. Further, the rotor rotates about a first axis. The second bore can further include a side surface, a plane perpendicular to the first axis that intersects both the side surface and the distal bearing surface. The drive shaft and the side surface of the second bore can operate together, against a common surface of the rotor, to prevent removal of the rotor from the second bore in a direction along the first axis.

10 Claims, 7 Drawing Sheets

U.S. PATENT DOCUMENTS

| | | | |
|---|---|---|---|
| 2,594,669 A * | 4/1952 | Calvert | 81/57.29 |
| 2,604,795 A * | 7/1952 | Ristow | 74/417 |
| 2,697,362 A * | 12/1954 | Keesling | 74/417 |
| 2,701,490 A * | 2/1955 | Griparis | 81/57.29 |
| 2,921,451 A * | 1/1960 | Helmke | 464/106 |
| 3,163,934 A * | 1/1965 | Wiseman | 433/115 |
| 3,509,629 A | 5/1970 | Kidokoro et al. | |
| 3,707,042 A * | 12/1972 | Talaga | 433/134 |
| 3,964,166 A | 6/1976 | Stahlman | |
| 4,053,983 A | 10/1977 | Flatland | |
| 4,266,933 A | 5/1981 | Warden et al. | |
| 4,403,679 A * | 9/1983 | Snider | 184/64 |
| 4,486,175 A | 12/1984 | Fisher et al. | |
| 4,522,595 A | 6/1985 | Selvidge | |
| 4,527,443 A * | 7/1985 | Ohoka | 74/417 |
| 4,604,058 A | 8/1986 | Fisher et al. | |
| 4,607,538 A * | 8/1986 | Geisthoff | 74/417 |
| 4,643,052 A * | 2/1987 | Badiali | 81/57.28 |
| 4,929,180 A | 5/1990 | Moreschini | |
| 4,944,677 A | 7/1990 | Alexandre | |
| 5,028,233 A | 7/1991 | Witherby | |
| 5,040,978 A | 8/1991 | Falcon et al. | |
| 5,062,796 A | 11/1991 | Rosenberg | |
| 5,083,922 A | 1/1992 | Yale | |
| 5,120,220 A * | 6/1992 | Butler | 433/125 |
| 5,131,846 A | 7/1992 | Hall | |
| 5,156,546 A | 10/1992 | Frank et al. | |
| 5,156,547 A | 10/1992 | Bailey | |
| 5,209,658 A | 5/1993 | Brahler | |
| 5,211,560 A | 5/1993 | Lowder et al. | |
| 5,273,559 A | 12/1993 | Hammar et al. | |
| 5,316,475 A | 5/1994 | Rosenberg | |
| 5,328,369 A | 7/1994 | Bailey | |
| 5,340,310 A | 8/1994 | Bifulk | |
| 5,348,473 A | 9/1994 | Kivlighan, Jr. | |
| 5,352,119 A * | 10/1994 | Sakurai | 433/125 |
| 5,360,339 A | 11/1994 | Rosenberg | |
| 5,374,189 A | 12/1994 | Mendoza | |
| 5,380,202 A | 1/1995 | Brahler | |
| 5,405,265 A | 4/1995 | Mendoza | |
| 5,423,679 A | 6/1995 | Bailey | |
| 5,433,605 A | 7/1995 | Strobl, Jr. | |
| 5,482,461 A | 1/1996 | Yale | |
| 5,484,284 A | 1/1996 | Bailey | |
| 5,496,218 A | 3/1996 | Brahler | |
| 5,503,555 A | 4/1996 | Bailey | |
| 5,507,644 A | 4/1996 | Kivlighan, Jr. | |
| 5,529,495 A | 6/1996 | Edwards | |
| 5,531,599 A | 7/1996 | Bailey | |
| 5,571,012 A | 11/1996 | Witherby et al. | |
| 5,584,690 A | 12/1996 | Maassarani | |
| 5,593,304 A | 1/1997 | Ram | |
| 5,645,426 A | 7/1997 | Grim et al. | |
| 5,683,247 A | 11/1997 | Bailey | |
| 5,690,488 A | 11/1997 | Spinello | |
| 5,692,901 A | 12/1997 | Roth et al. | |
| 5,730,595 A | 3/1998 | Bailey | |
| 5,743,718 A | 4/1998 | Mendoza et al. | |
| 5,749,728 A | 5/1998 | Bailey | |
| 5,766,008 A | 6/1998 | Hughes | |
| 5,775,905 A | 7/1998 | Weissenfluh et al. | |
| 5,797,744 A | 8/1998 | Rosenberg | |
| 5,871,353 A | 2/1999 | Pierce et al. | |
| 5,876,203 A | 3/1999 | Bailey | |
| 5,902,107 A | 5/1999 | Lowell | |
| 5,911,577 A | 6/1999 | Henrikson | |
| 5,964,590 A | 10/1999 | Loddeke et al. | |
| 6,012,922 A | 1/2000 | Novak | |
| 6,053,732 A | 4/2000 | Sale | |
| 6,083,000 A | 7/2000 | Charlton | |
| 6,089,866 A | 7/2000 | Brahler | |
| 6,099,309 A | 8/2000 | Cardarelli | |
| 6,146,140 A | 11/2000 | Bailey | |
| 6,149,430 A | 11/2000 | Nemetz et al. | |
| 6,168,433 B1 | 1/2001 | Hamlin | |
| 6,187,294 B1 | 2/2001 | Penner | |
| 6,203,322 B1 | 3/2001 | Kraenzle | |
| 6,247,931 B1 | 6/2001 | Postal et al. | |
| 6,257,886 B1 | 7/2001 | Warner | |
| 6,302,692 B1 | 10/2001 | Pond et al. | |
| 6,305,935 B1 | 10/2001 | Cardarelli | |
| 6,315,559 B1 | 11/2001 | Nakanishi | |
| 6,382,971 B1 | 5/2002 | Randolph | |
| 6,409,507 B1 | 6/2002 | Postal et al. | |
| 6,527,552 B2 | 3/2003 | Loddeke et al. | |
| 6,632,090 B1 | 10/2003 | Randolph | |
| 6,821,119 B2 | 11/2004 | Shortt et al. | |
| 6,875,017 B1 | 4/2005 | Tarr | |

\* cited by examiner

PROPHY ANGLE

CROSS-REFERENCE TO RELATED APPLICATION

This application is a Continuation of U.S. application Ser. No. 11/189,193, filed Jul. 26, 2005, now U.S. Pat. No. 7,422,433, which is incorporated herein by reference in its entirety.

STATEMENT REGARDING FEDERALLY SPONSORED RESEARCH OR DEVELOPMENT

N/A

FIELD OF THE INVENTION

The present invention relates to dental instruments, and more particularly to dental prophylaxis devices.

BACKGROUND OF THE INVENTION

Dental prophylaxis angles, generally referred to as "prophy angles," are commonly used dental instruments providing rotation for dental tools such as brushes, prophy cups, or other receptacles used in polishing teeth. A prophy angle typically includes a housing having a neck and a head portion extending at approximately a 90° angle to the neck, which increases the ability of a dentist to reach various surfaces of the teeth of a patient. A drive shaft can be located within the housing and attached to a driven gear in the head of the prophy angle. Prophy angles are generally affixed to a handpiece, which connects the prophy angle to a drive source, thereby enabling a rotating motion of the drive shaft and driven gear of the prophy angle and any affixed dental tool.

Prophy angles are commonly manufactured from lightweight plastic to make them disposable and thereby increasing overall sterility in the dental environment. One drawback of these current instruments is that they are often cumbersome to assemble and may contain a myriad of loosely fitting parts. For example, prior prophy angles have included a two-piece housing which must be mated together prior to use to enclose the inner components of the angle. During use of the prophy angle, the housing may experience increased strain when in contact with the teeth of a patient, and cause the seams in the housing to separate and expose the inner components of the angle. Such separation in the housing may result in a spacing apart or separation of the internal gears of the angle, potentially leading to failure of the device.

In addition to concerns regarding housing integrity, the drive shaft and driven gear of an angle may experience some displacement during use of the prophy angle. As the angle is being used, the drive shaft may excessively move forward or backward due to an increase in the pressure placed on the rotating parts, and result either in an increased amount of force between the gear teeth of the drive shaft and the driven gear, or separation of engagement of the gear teeth of the shaft from those of the driven gear. Subsequently, this displacement can also lead to a premature malfunction of the prophy angle prior to completing a dental procedure.

Furthermore, conventional prophy angles may have a significant amount of contact between surfaces of the housing, the drive shaft and the driven gear. Such large, often flat surfaces can generate increasing amounts of friction as the prophy angle is used at higher rates of rotation. The increased friction can prevent the prophy angle from reaching the desired rate of rotation, may cause enhanced wear and tear between the interacting components, and may generate greater heat, thus making the angle uncomfortable to use.

In light of the above limitations, it would be desirable to provide a prophy angle having a singular housing, where the prophy angle limits displacement of the internal components during use, and further reduces friction between interacting surfaces.

SUMMARY OF THE INVENTION

The present invention advantageously provides a dental prophylaxis angle having a housing, a drive shaft, and a rotor. In one embodiment, the housing can include a first bore and a second bore in communication with the first bore. The drive shaft is positionable in the first bore and can include a distal bearing surface. The drive shaft can drive the rotor. The rotor can be disposed within the second bore and can rotate about a first axis. The second bore can further include a side surface, a plane perpendicular to the first axis that intersects both the side surface and the distal bearing surface. The drive shaft and the side surface of the second bore can operate together, against a common surface of the rotor, to prevent removal of the rotor from the second bore in a direction along the first axis.

In another embodiment, a prophy angle can include a housing defining a first bore and a second bore in communication with the first bore, a rotor disposed within the second bore, and a drive shaft driving the rotor. The second bore can include a side surface. The drive shaft can include a portion positioned adjacent to the rotor. The rotor can include a bearing surface about a circumference of the rotor positioned adjacent to both the portion of the drive shaft and the side surace of the second bore. The side surface of the second bore and the portion positioned adjacent to the rotor can operate together against the bearing surface to prevent removal of the rotor from the second bore.

In yet a different embodiment, a dental prophylaxis angle can include a housing defining a first bore and a second bore, each of the bores defining a cavity with the second bore being positioned at an angle with respect to the first bore. A rotor disposed within the second bore that rotates about a first axis as well as a drive shaft that drives the rotor. The drive shaft can be disposed within the first bore. The second bore can include an opening at one end, a back wall at an opposite end, and a sidewall therebetween and a multiplicity of ribs. The multiplicity of ribs can extend from the back wall of the second bore towards the opening of the second bore and from the sidewall toward the interior of the cavity of the second bore. The drive shaft and the multiplicity of ribs operate together, against a common surface of the rotor, to prevent removal of the rotor from the second bore in a direction along the first axis.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
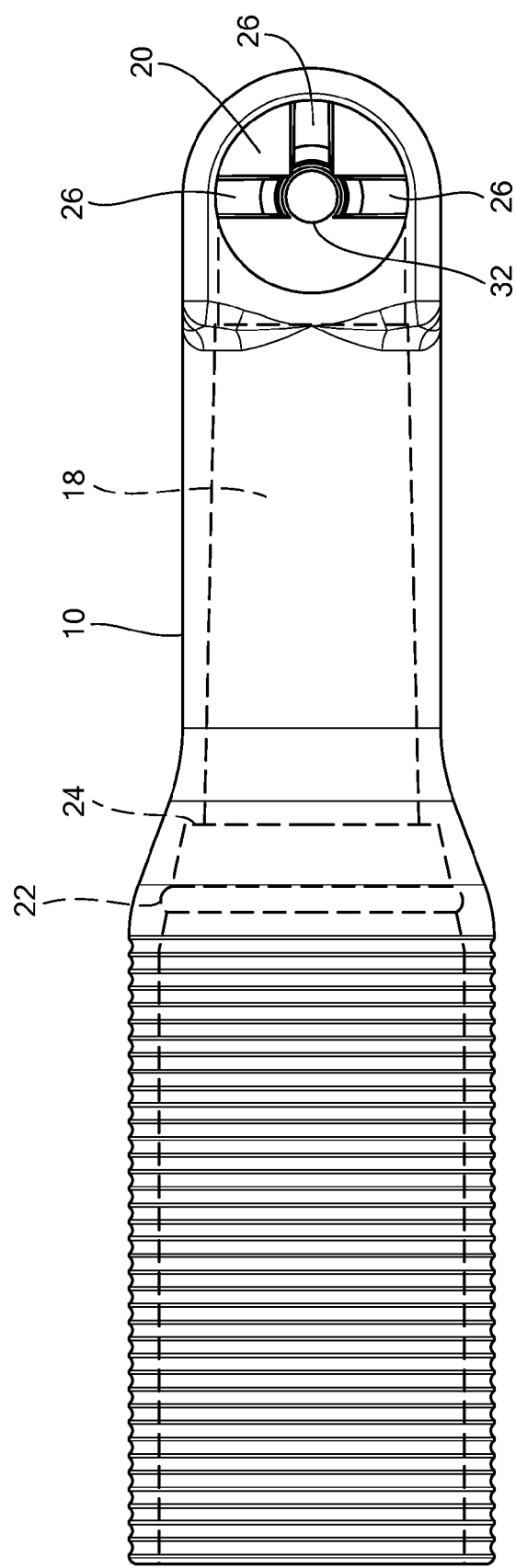
FIG. 1 shows a top view of a housing in accordance with the present invention.
Figure 2:
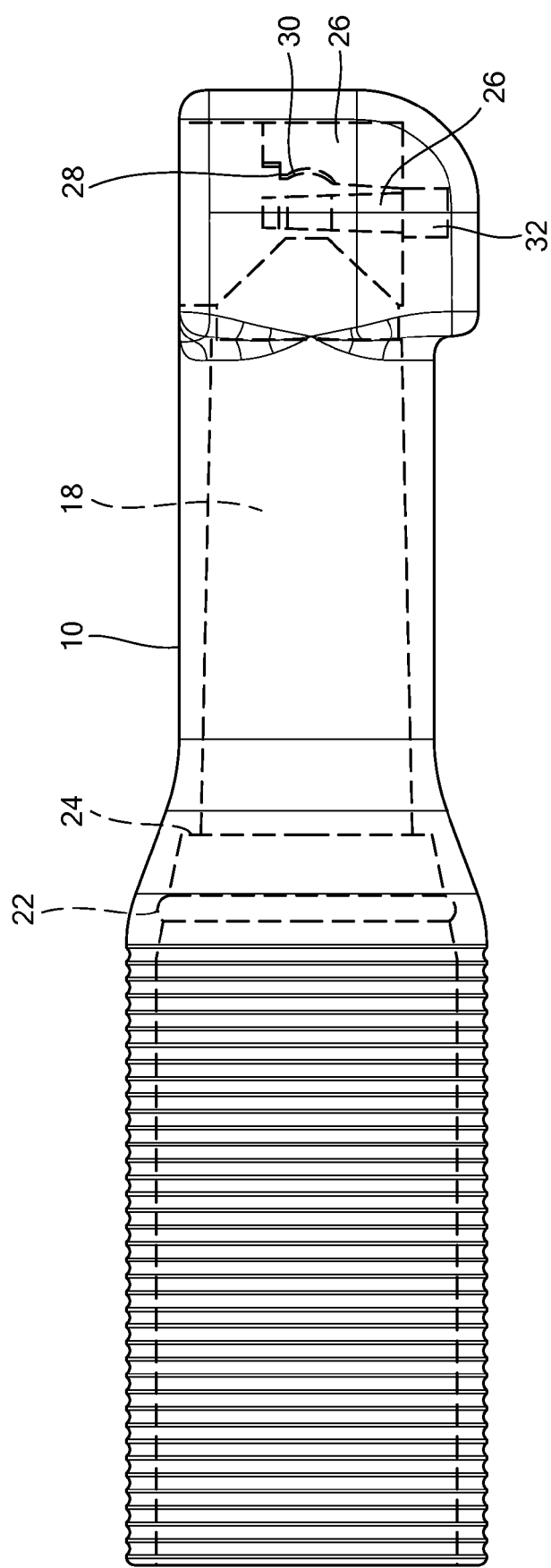
FIG. 2 illustrates a side view of a housing in accordance with the present invention.

In an exemplary embodiment, the present invention provides a dental prophylaxis angle having a singular housing 10, a drive shaft 12, a rotor 14, and a collar 16. FIGS. 1 and 2 illustrate the singular housing 10 as a one-piece element which defines a first bore 18 extending through a length of the housing 10. A second bore 20 is in communication with and extends from the first bore 18 at a substantially perpendicular angle. The housing 10 further defines an annular groove 22 circumscribing a portion of the first bore 18, and a housing shoulder 24 disposed about a portion of the first bore 18 where the first bore 18 decreases in diameter.

A plurality of rotor bearing elements 26 is radially positioned within the second bore 20. Each rotor bearing element 26 includes an upper bearing surface 28, as well as having a spherical recess 30 on a surface of the bearing element that is substantially perpendicular to the upper bearing surface 28. In addition, the housing 10 includes a third bore 32 that is substantially coaxial with the second bore 20, yet having a diameter substantially less then the diameter of the second bore 20. The housing 10 can be constructed from a variety of available plastics having sufficient rigidity to apply pressure to a patient's teeth, while remaining flexible enough to receive the internal components of the prophy angle.

Figure 3:
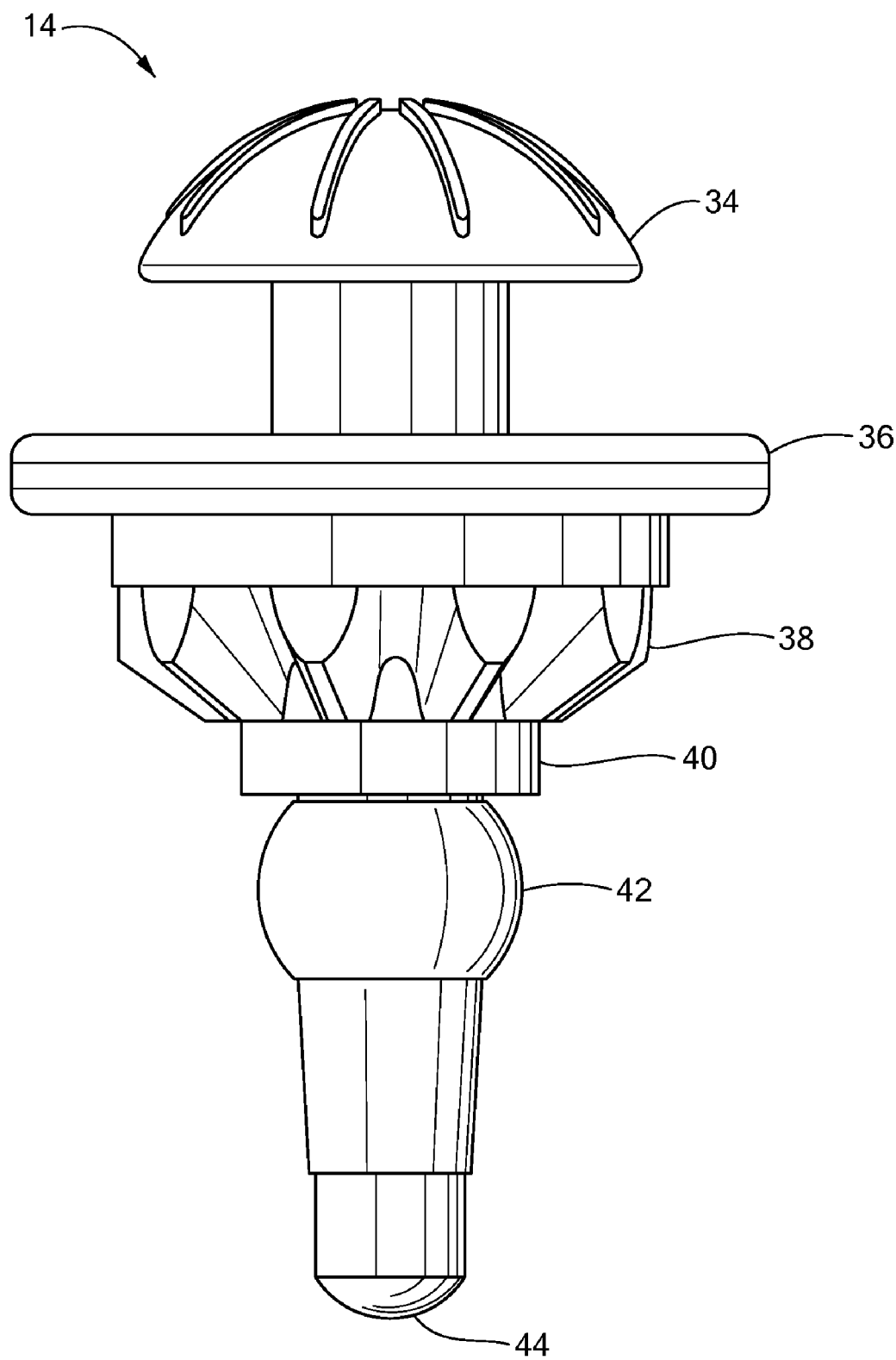
FIG. 3 depicts a rotor in accordance with the present invention.

As shown in FIG. 3, the rotor 14 includes a button 34 disposed at one end, to provide, e.g., attachment of a prophy cup (not shown). The button 34 may include additional protrusions to accommodate a specific prophy cup, but is not limited to a specific shape or orientation. The rotor 14 further includes a radially-extending flange 36, a plurality of driven gear teeth 38, and an intermediate disc 40 radially disposed about a center axis of the rotor 14. Moreover, a spherical bearing 42 is included along a length of the rotor 14, in addition to a spherical tip 44 at an end of the rotor 14 opposite the button 34.

Figure 4:
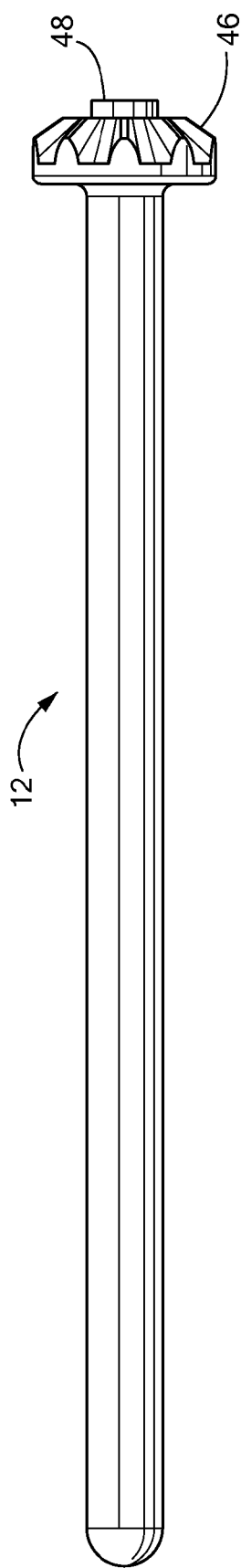
FIG. 4 shows a side view of a drive element in accordance with the present invention.
Figure 5:
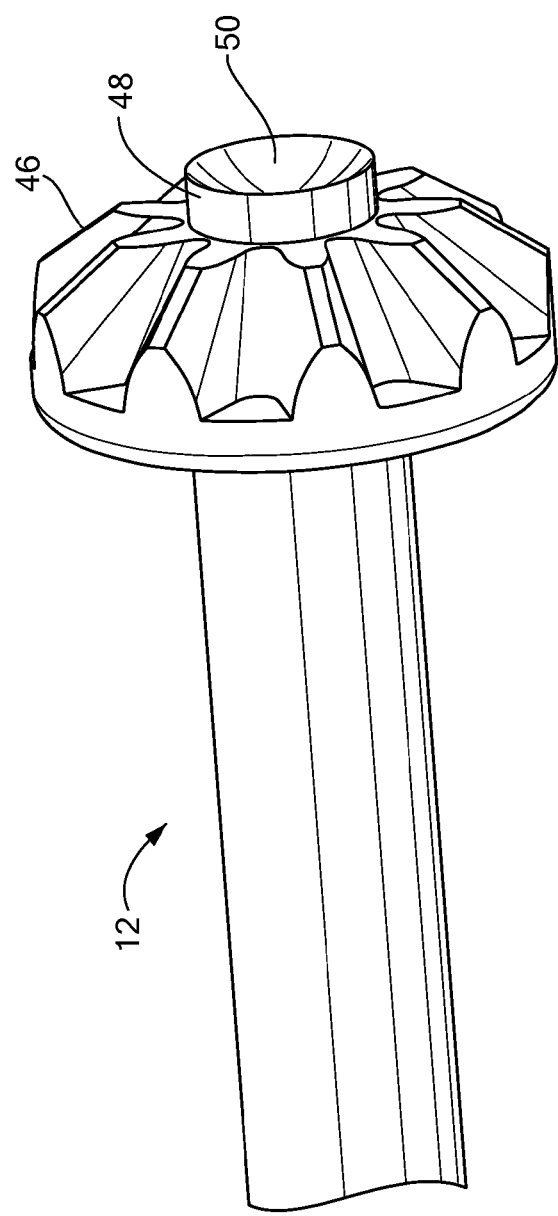
FIG. 5 illustrates an angled view of a drive element in accordance with the present invention.
Figure 6:
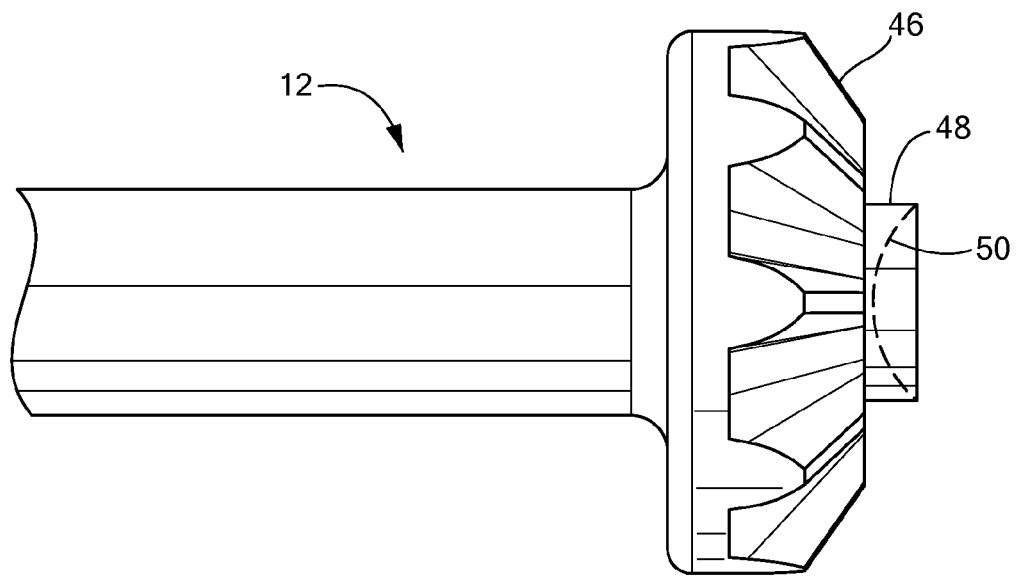
FIG. 6 depicts a side view of a drive element in accordance with the present invention.

In FIGS. 4 through 6, the drive shaft 12 is shown as an elongate body having a plurality of drive gear teeth 46 disposed at one end. A post 48 extends shortly beyond the plurality of drive gears 46, with the post 48 having a spherical depression 50 on an end surface.

Figure 7:
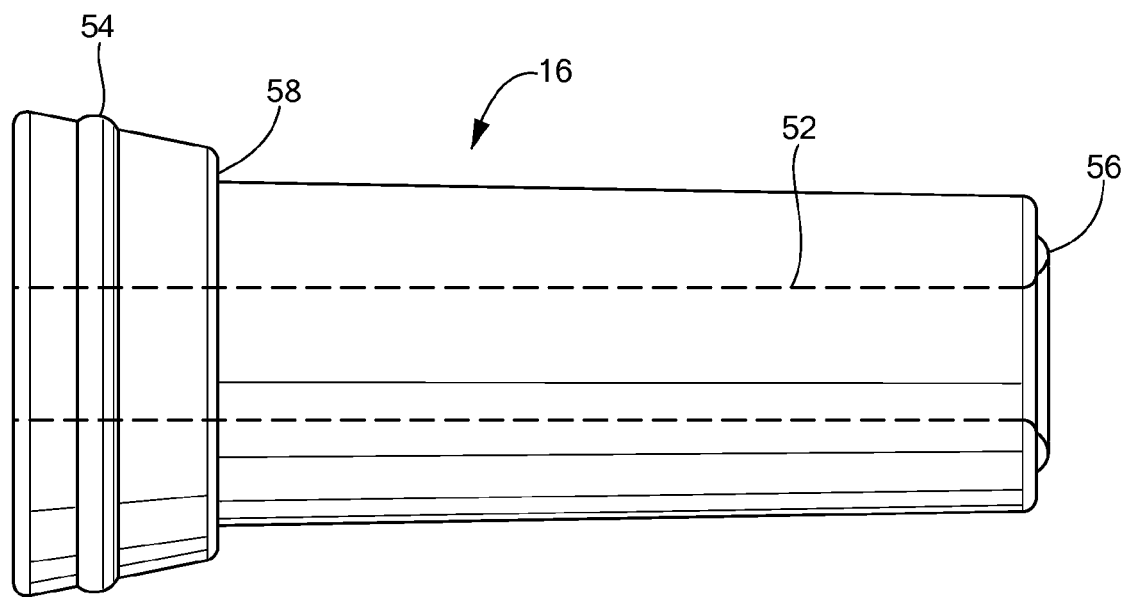
FIG. 7 illustrates a collar in accordance with the present invention.

Now referring to FIG. 7, the present invention includes the collar 16, where the collar 16 defines an axial bore 52 extending throughout the length of the collar 16. The collar 16 also includes a protruding first annular wall 54 circumscribing a portion of the collar 16 proximate a first end of the collar 16. A second annular wall 56 circles the axial bore 52 at a second end surface opposite the first end of the collar 16. Both the first and second annular walls may include semi-circular cross sections, e.g., the protruding walls may have rounded surfaces. In addition, the collar 16 defines a collar shoulder 58 disposed about a portion of the collar 16 where the exterior diameter of the collar 16 decreases.

Figure 8:
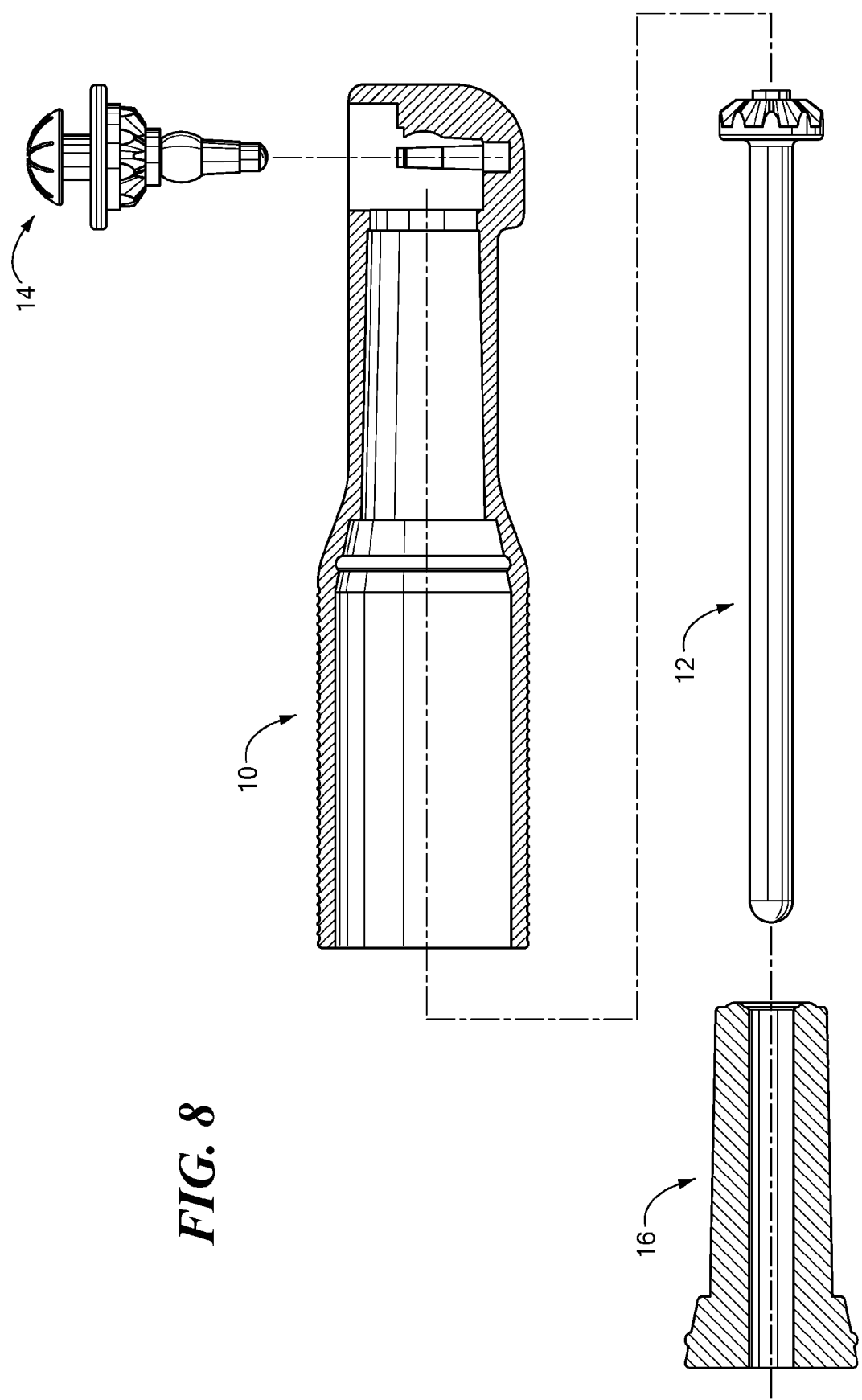
FIG. 8 shows an assembly view of a prophy angle in accordance with the present invention.
Figure 9:
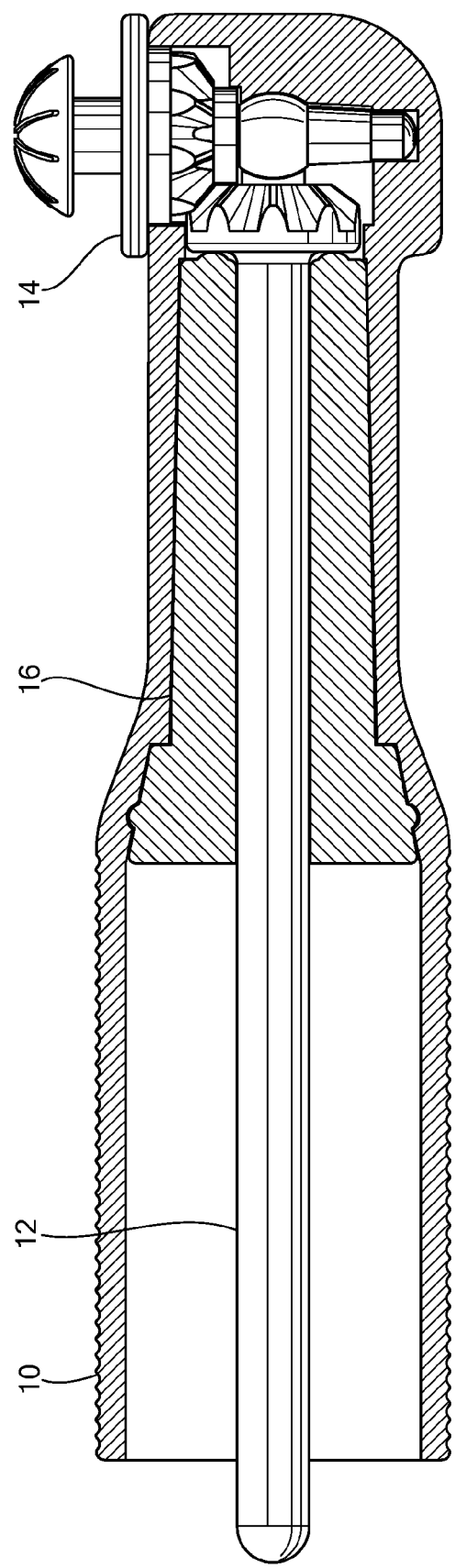
FIG. 9 shows an assembled prophy angle in accordance with the present invention.

As shown in FIG. 8, the prophy angle of the present invention is shown in an exploded assembly view to illustrate the placement and interaction of the components. In this embodiment, the rotor 14 is positioned within the second bore 20 of the singular housing 10 with the spherical tip 44 of the rotor 14 extending downward into the third bore 32 of the housing 10. Because of the spherical nature of the rotor 14 tip, there is minimal contact between the rotor 14 and the lower surface of the third bore 32 as compared to a traditional tip having a flat surface. As such, friction between the spherical tip 44 and the housing 10 is reduced significantly at this contact point. Moreover, during use, the spherical tip 44 acts to transmit high thrust loads experienced by the rotor 14 to the housing 10, thereby reducing the loads experienced between the meshed gears of the rotor 14 and the drive shaft 12.

The spherical bearing 42 of the rotor 14 is received by the spherical recess 30 of each of the plurality of rotor bearing elements 26, with the intermediate disc 40 being located proximate to the upper bearing surface 28 of each of the plurality of rotor bearing elements 26. Of note, it is not necessary that the curvature of the spherical bearing or the curvature of the spherical recesses are indeed substantially spherical. Rather, it is intended that the curvature of the spherical bearing is substantially similar to the curvature of the recess in the rotor bearing elements, whether the curved surfaces are precisely spherical, ovoidal, elliptical or otherwise.

The flange 36 of the rotor 14 rests over the opening of the second bore 20, effectively preventing any debris from entering the interior of the housing 10, which could potentially interfere with the subsequent operation of the prophy angle, while the button 34 for a prophy cup (not shown) remains exposed to the exterior of the housing 10.

Subsequent to the placement of the rotor 14, the drive shaft 12 is inserted into the first bore 18 of the housing 10 such that the plurality of drive gear teeth 46 of the drive shaft 12 engages the plurality of driven gear teeth 38 of the rotor 14. In addition, the spherical depression 50 on the post 48 of the drive shaft 12 abuts the spherical bearing 42 of the rotor 14. While in general operation, the contact between the spherical depression 50 of the drive shaft 12 and the spherical bearing 42 of the rotor 14 may be minimal. However, should the drive shaft 12 experience any displacement or increased pressure against the rotor 14, the rotor 14 will transmit the additional force to the housing 10 through the spherical recesses 30 of the plurality of rotor bearing elements 26. By transferring the force to the housing 10, the likelihood that the increased force will cause the gears of the drive shaft 12 and the rotor 14 to seize is significantly reduced.

Next, the collar 16 is positioned in the second bore 20 of the housing 10 such that a portion of the drive shaft 12 is located within the axial bore 52 of the collar 16. The collar 16 is placed within the housing 10 and moved towards the direction of the rotor 14 until the collar shoulder 58 abuts the housing shoulder 24. Moreover, the second annular wall 56 of the collar 16 abuts an underside of the plurality of drive gear teeth at a rear shoulder, providing a rounded bearing surface of the collar 16 in contact with the drive shaft 12. The rounded surface of the second annular wall 56 reduces the contact area between the collar 16 and the drive shaft 12, thereby reducing friction as compared to traditional flat contact surface areas.

In this position, the first annular wall 54 of the collar 16 couples with the annular groove 22 of the housing 10, thereby securing the collar 16 in the housing 10. As a result, the collar 16 secures the drive shaft 12 in engagement with the rotor 14, which is further supported and secured by the plurality of rotor bearing elements 26 in the second bore 20 of the housing 10. These features of the prophy angle significantly reduce and may altogether prevent any displacement of the drive shaft 12 or rotor 14 while the prophy angle is being used.

The prophy angle of the present invention provides an easily assembled dental device having features which secure the inner components against displacement during use, as well as providing numerous rounded surfaces which reduce friction experienced between moving parts by reducing the contacting surface areas.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A dental prophylaxis angle, comprising:
a housing defining a first bore and a second bore in communication with the first bore;
a rotor disposed within the second bore and rotating about a first axis; and
a drive shaft driving the rotor and positioned within the first bore, the drive shaft including a distal bearing surface, wherein
the second bore includes a side surface, a plane perpendicular to the first axis intersects both the side surface and the distal bearing surface;
the drive shaft and the side surface of the second bore operating together, against a common surface of the rotor, to prevent removal of the rotor from the second bore in a direction along said first axis.

2. The dental prophylaxis angle of claim 1, wherein the common surface of the rotor includes a bearing surface about a circumference of the rotor and the bearing surface engages the side surface of the second bore.

3. The dental prophylaxis angle of claim 2, wherein the distal bearing surface of the drive shaft engages the bearing surface of the rotor.

4. The dental prophylaxis angle of claim 2, wherein the bearing surface of the rotor is convex and the side surface of the second bore and the distal bearing surface of the drive shaft are concave.

5. The dental prophylaxis angle of claim 4, wherein the bearing surface of the rotor, the distal bearing surface of the drive shaft, and the side surface of the second bore are substantially spherical.

6. The dental prophylaxis angle of claim 2, wherein the housing includes a plurality of inwardly extending ribs positioned in the second bore and
each of the ribs includes a portion of the side surface of the second bore.

7. A dental prophylaxis angle, comprising:
a housing defining a first bore and a second bore in communication with the first bore;
a rotor disposed within the second bore; and
a drive shaft driving the rotor, wherein
the second bore includes a side surface,
the drive shaft includes a portion positioned adjacent to the rotor,
the rotor includes a bearing surface about a circumference of the rotor positioned adjacent both the portion of the drive shaft and the side surface of the second bore, and
the side surface of the second bore and the portion operating together against the bearing surface to prevent removal of the rotor from the second bore.

8. A dental prophylaxis angle, comprising:
a housing defining a first bore and a second bore, each of the bores defining a cavity, the second bore being positioned at an angle with respect to the first bore;
a rotor disposed within the second bore and rotating about a first axis; and,
a drive shaft driving the rotor, the drive shaft disposed within the first bore,
wherein the second bore includes an opening at one end, a back wall at an opposite end, and a sidewall therebetween and a multiplicity of ribs, the multiplicity of ribs extending from the back wall of the second bore towards the opening of the second bore and from the sidewall toward the interior of the cavity of the second bore
and wherein the drive shaft and the multiplicity of ribs operating together, against a common surface of the rotor, to prevent removal of the rotor from the second bore in a direction along said first axis.

9. The dental prophylaxis angle of claim 8, wherein each of the multiplicity of ribs are positioned perpendicular from the sidewall.

10. The dental prophylaxis angle of claim 8, wherein the angle between the first bore and the second bore is about ninety degrees.

* * * * *